United States Patent
Thaning et al.

(10) Patent No.: US 8,951,502 B2
(45) Date of Patent: *Feb. 10, 2015

(54) METHOD OF DYNAMIC NUCLEAR POLARISATION (DNP)

(75) Inventors: Mikkel Thaning, Tygelsjo (NO); Rolf Servin, Malmo (SE)

(73) Assignee: GE Healthcare AS, Oslo (NO)

(*) Notice: Subject to any disclaimer, the term of this patent is extended or adjusted under 35 U.S.C. 154(b) by 1059 days.

This patent is subject to a terminal disclaimer.

(21) Appl. No.: 12/095,169

(22) PCT Filed: Dec. 1, 2006

(86) PCT No.: PCT/NO2006/000449
§ 371 (c)(1),
(2), (4) Date: May 28, 2008

(87) PCT Pub. No.: WO2007/064226
PCT Pub. Date: Jun. 7, 2007

(65) Prior Publication Data
US 2008/0260649 A1 Oct. 23, 2008

(30) Foreign Application Priority Data

Dec. 1, 2005 (NO) .................... 20055681
Dec. 2, 2005 (NO) .................... 20055705
Jul. 5, 2006 (NO) .................... 20063119

(51) Int. Cl.
A61K 49/06 (2006.01)
A61K 49/20 (2006.01)
A61K 49/10 (2006.01)
A61K 49/12 (2006.01)

(52) U.S. Cl.
CPC ............. *A61K 49/20* (2013.01); *A61K 49/10* (2013.01); *A61K 49/124* (2013.01)
USPC ...................................... 424/9.36

(58) Field of Classification Search
None
See application file for complete search history.

(56) References Cited

U.S. PATENT DOCUMENTS

| | | | |
|---|---|---|---|
| 4,969,184 A | 11/1990 | Gordon et al. | |
| 5,314,681 A * | 5/1994 | Leunbach et al. | 424/9.32 |
| 5,985,244 A * | 11/1999 | Unger | 424/9.3 |
| 6,278,893 B1 | 8/2001 | Ardenkjaer-Larson et al. | |
| 6,311,086 B1 * | 10/2001 | Ardenkjaer-Larsen et al. | 600/420 |
| 2004/0039281 A1 | 2/2004 | Cook et al. | |
| 2005/0063491 A1 | 3/2005 | Saloka | |
| 2008/0043731 A1 | 2/2008 | Lim et al. | |

FOREIGN PATENT DOCUMENTS

| | | |
|---|---|---|
| EP | 0375074 | 6/1990 |
| GB | 2252245 | 8/1992 |
| JP | 05506128 A | 9/1993 |
| JP | H05-506428 A | 9/1993 |
| JP | 2002501006 A | 1/2002 |
| JP | 2004503786 A | 2/2004 |
| JP | 2007523504 A | 8/2007 |
| JP | 2007523506 A | 8/2007 |
| WO | 9000904 A1 | 2/1990 |
| WO | 91/12024 | 8/1991 |
| WO | 96/39367 | 12/1996 |
| WO | 9839277 A1 | 9/1998 |
| WO | 99/35508 | 7/1999 |
| WO | 03/089656 | 10/2003 |
| WO | 2005/024440 | 3/2005 |
| WO | 2006/011809 | 2/2006 |

OTHER PUBLICATIONS

Wolber J, Ellner F, Fridlund B, Gram A, Johannesson H, Hansson G, Hansson LH, Lerche MH, Mansson S, Servin R, Thaning M, Golman K, Ardenkjaer-Larsen JH. Generating highly polarized nuclear spins in solution using dynamic nuclear polarization. 2004 Nucl. Instrum. Methods Phys. Res. A 526: 173-181.*

JP Office Action dated Apr. 3, 2012 from corresponding JP Application No. 2008-543224.

* cited by examiner

*Primary Examiner* — Michael G Hartley
*Assistant Examiner* — Jennifer Lamberski
(74) *Attorney, Agent, or Firm* — Jean K. Testa

(57) ABSTRACT

The invention relates to a method of dynamic nuclear polarisation (DNP) using a combination of a trityl radical and a paramagnetic metal ion as the polarising agent leading to enhanced levels of polarisation in the sample to be polarised and to compositions and polarising agents for use in the method.

4 Claims, No Drawings

METHOD OF DYNAMIC NUCLEAR POLARISATION (DNP)

This application is a filing under 35 U.S.C. 371 of international application number PCT/NO2006/000449, filed Dec. 1, 2006, which claims priority to application number 20055681 filed Dec. 1, 2005; 20055705 filed Dec. 2, 2005 and 20063119 filed Jul. 5, 2006 in Norway the entire disclosure of which is hereby incorporated by reference.

The invention relates to a method of dynamic nuclear polarisation (DNP) leading to enhanced levels of polarisation in the sample to be polarised and to compositions and polarising agents for use in the method.

Magnetic resonance (MR) imaging (MRI) is a imaging technique that has become particularly attractive to physicians as it allows for obtaining images of a patient's body or parts thereof in a non-invasive way and without exposing the patient and the medical personnel to potentially harmful radiation such as X-ray. Because of its high quality images, MRI is the favourable imaging technique of soft tissue and organs and it allows for the discrimination between normal and diseased tissue, for instance tumours and lesions.

MRI may be carried out with or without MR contrast agents. However, contrast-enhanced MRI usually enables the detection of much smaller tissue changes which makes it a powerful tool for the detection of early stage tissue changes like for instance small tumours or metastases.

Several types of contrast agents have been used in MRI. Water-soluble paramagnetic metal chelates, for instance gadolinium chelates like Omniscan™ (GE Healthcare) are widely used MR contrast agents. Because of their low molecular weight they rapidly distribute into the extracellular space (i.e. the blood and the interstitium) if administered into the vasculature. They are also cleared relatively rapidly from the body.

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours for example as a result of angiogenesis.

Despite the undisputed excellent properties of the aforementioned contrast agents their use is not without any risks. Although paramagnetic metal chelate complexes have usually high stability constants, it is possible that toxic metal ions are released in the body after administration. Further, these type of contrast agents show poor specificity.

WO-A-99/35508 discloses a method of MR investigation of a patient using a hyperpolarised solution of a high $T_1$ agent as MRI contrast agent. The term "hyperpolarisation" means enhancing the nuclear polarisation of NMR active nuclei present in the high $T_1$ agent, i.e. nuclei with non-zero nuclear spin, preferably $^{13}$C- or $^{15}$N-nuclei, to a level over that found at room temperature and 1 T (thermal polarisation). Upon enhancing the nuclear polarisation of NMR active nuclei, the population difference between excited and ground nuclear spin states of these nuclei is significantly increased and thereby the MR signal intensity is amplified by a factor of hundred and more. When using a hyperpolarised $^{13}$C- and/or $^{15}$N-enriched high $T_1$ agent, there will be essentially no interference from background signals as the natural abundance of $^{13}$C and/or $^{15}$N is negligible and thus not only the signal intensity but also the image contrast will be advantageously high. The main difference between conventional MRI contrast agents and hyperpolarised high $T_1$ agents is that in the former changes in contrast are caused by affecting the relaxation times of water protons in the body whereas the latter class of agents can be regarded as non-radioactive tracers, as the MR signal obtained arises solely from the injected agent.

A variety of possible high $T_1$ agents suitable for use as MR imaging agents are disclosed in WO-A-99/35508 including but not limited to non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulphonamides. It is further stated that intermediates in metabolic cycles such as the citric acid cycle like fumaric acid are preferred imaging agents for MR imaging of metabolic activity.

It has to be stressed that the signal of a hyperpolarised imaging agent decays due to relaxation and—upon administration to the patient's body—dilution. Hence the $T_1$ value of the imaging agents in biological fluids (e.g. blood) must be sufficiently long (high) to enable the agent to be distributed to the target site in the patient's body in a highly hyperpolarised state. Apart from the imaging agent having a high $T_1$ value, it is extremely favourable to achieve a high polarisation level.

Several methods for obtaining hyperpolarised high $T_1$ agents are disclosed in WO-A-99/35508; one of them is the dynamic nuclear polarisation (DNP) technique whereby polarisation of a sample is effected by a polarising agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of DNP agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01/96895, both of which are included by reference herein.

The DNP agent plays a decisive role in the DNP process as its choice has a major impact on the level of polarisation that can be achieved in the sample to be polarised. A variety of DNP agents—in WO-A-99/35508 denoted "OMRI contrast agents"—is known. The use of oxygen-based, sulphur-based or carbon-based stable trityl radicals as described in WO-A-99/35508, WO-A-88/10419, WO-A-90/00904, WO-A-91/12024, WO-A-93/02711 or WO-A-96/39367 has resulted in high levels of polarisation in a variety of different samples.

We have now surprisingly found that the addition of paramagnetic metal ions to a composition comprising a sample to be polarised by the DNP method and a trityl radical as DNP agent results in a remarkably increased polarisation level in the sample. This is especially favourable in a clinical situation where the polarised sample is used as an MR imaging agent in an MR examination procedure of a patient. If the polarisation level in the sample could be for instance enhanced by a factor 2, only half of the concentration of the sample has to be used in the MR examination procedure. This is of course advantageous not only from an economical perspective but also opens the possibility to use samples which would have unwanted side effects at these double concentrations.

Thus, viewed from one aspect, the present invention provides a method of producing a solid hyperpolarised sample comprising preparing a composition comprising the sample, a trityl radical and a paramagnetic metal ion and carrying out dynamic nuclear polarisation on the composition.

The terms "hyperpolarised" and "polarised" are used interchangeably hereinafter and denote a nuclear polarisation level in excess. Preferably, the terms "hyperpolarised" and "polarised" denote a nuclear polarisation level in excess of 0.1%, more preferably in excess of 1% and most preferably in excess of 10%.

The level of polarisation may for instance be determined by solid state NMR measurements of the NMR active nucleus in the hyperpolarised sample. For instance, if the NMR active nucleus in the hyperpolarised sample is $^{13}$C, a solid state $^{13}$C-NMR of said sample is acquired. The solid state $^{13}$C-NMR measurement preferably consists of a simple pulse-acquire NMR sequence using a low flip angle. The signal intensity of the hyperpolarised sample is compared with the polarisation level of the sample before the dynamic nuclear polarisation process. The level of polarisation is then calculated from the ratio of the signal intensities of sample before and after DNP.

In a similar way, the level of polarisation for dissolved hyperpolarised samples may be determined by liquid state NMR measurements of the NMR active nucleus in the hyperpolarised sample. Again the signal intensity of the dissolved hyperpolarised sample is compared with the polarisation level of the dissolved sample before the dynamic nuclear polarisation process. The level of polarisation is then calculated from the ratio of the signal intensities of sample before and after DNP.

The term "sample" denotes the molecular entity or entities to be hyperpolarised by dynamic nuclear polarisation (DNP). Generally, the sample is one or more chemical compounds.

The method according to the invention leads to high polarisation levels in the sample to be polarised. In principle every chemical compound can be used as the sample in the method of the invention. In a preferred embodiment, the sample is a drug candidate, suitably a small organic molecule, e.g. less than 2000 Da, or a mixture of several drug candidates and the hyperpolarised drug candidate(s) may be used in NMR assays for instance to determine binding affinity to a certain receptor or in enzyme assays. Such assays are described in WO-A-2003/089656 or WO-A-2004/051300 and they are preferably based on the use of liquid state NMR spectroscopy which means that the hyperpolarised solid sample has to be liquefied after polarisation, preferably by dissolving or melting it. The sample may or may not be isotopically enriched.

In another preferred embodiment, the sample is an imaging agent or a precursor thereof and the hyperpolarised sample is used as imaging agent in MR imaging and/or chemical shift imaging. Preferred samples are those which contain polarised nuclei that exhibit slow longitudinal relaxation so that polarisation is maintained for a sufficient length of time for transfer into an organism and subsequent imaging. Preferred samples contain nuclei with longitudinal relaxation time constants ($T_1$) that are greater than 10 seconds, preferably greater than 30 seconds and even more preferably greater that 60 seconds. Such so called "high $T_1$ agents" are for instance described in WO-A-99/35508. Alternatively, $T_1$ values of possible samples may be found in the literature or may be determined by acquiring an NMR spectrum of the possible sample, e.g. a $^{13}$C-NMR spectrum to determine the $T_1$ of a $^{13}$C-labelled possible sample.

Especially preferred samples are samples that play a role in the metabolic processes in the human and non-human animal body. Such hyperpolarised imaging agents can be used to get information about the metabolic state of a tissue in an in vivo MR investigation, i.e. they are useful for in vivo MR imaging of metabolic activity. Information of the metabolic status of a tissue might for instance be used to discriminated between healthy (normal) and diseased tissue. Especially preferred samples are thus endogenous compounds, more preferably endogenous compounds that play a role in a metabolic process in the human or non-human animal body. Especially preferred samples selected from amino acids (in protonated or deprotonated form), preferably alanine, glycine, glutamine, glutamic acid, cysteine, asparagine and aspartic acid, acetate, pyruvic acid, pyruvate, oxalate, malate, fumarate, lactate, lactic acid, citrate, bicarbonate, malonate, succinate, oxaloacetate, α-ketoglutarate, 3-hydroxybutyrate, isocitrate and urea. In a very preferred embodiment, the aforementioned preferred samples are isotopically enriched, more preferably $^{13}$C- or $^{15}$N-isotopically enriched, most preferred $^{13}$C-isotopically enriched.

Generally, a sample intended to be used as an MR imaging agent is preferably an isotopically enriched compound, the isotopic enrichment being an isotopic enrichment of non-zero spin nuclei (MR active nuclei), suitably $^{15}$N and/or $^{13}$C, more preferably $^{13}$C. The isotopic enrichment may include either selective enrichments of one or more sites within the compound molecule or uniform enrichment of all sites. Enrichment can for instance be achieved by chemical synthesis or biological labelling, both methods are known in the art and appropriate methods may be chosen depending on the compound to be isotopically enriched.

A preferred embodiment of a sample that is intended to be used as an MR imaging agent is a sample that is isotopically enriched in only one position of the molecule, preferably with an enrichment of at least 10%, more suitably at least 25%, more preferably at least 75% and most preferably at least 90%. Ideally, the enrichment is 100%.

The optimal position for isotopic enrichment is dependent on the relaxation time of the MR active nuclei. Preferably, compounds are isotopically enriched in positions with long $T_1$ relaxation time. $^{13}$C-enriched compounds that are enriched at a carboxyl-C-atom, a carbonyl-C-atom or a quaternary C-atom are preferably used.

In a preferred embodiment, pyruvic acid or pyruvate is used as a sample in the method of the invention. Pyruvic acid and pyruvate may be isotopically enriched at the C1-position ($^{13}$C$_1$-pyruvic acid/-pyruvate), at the C2-position ($^{13}$C$_2$-pyruvic acid/-pyruvate), at the C3-position ($^{13}$C$_3$-pyruvic acid/-pyruvate), at the C1- and the C2-position ($^{13}$C$_{1,2}$-pyruvic acid/-pyruvate), at the C1- and the C3-position ($^{13}$C$_{1,3}$-pyruvic acid/-pyruvate), at the C2- and the C3-position ($^{13}$C$_{2,3}$-pyruvic acid/-pyruvate) or at the C1-, C2- and C3-position ($^{13}$C$_{1,2,3}$-pyruvic acid/-pyruvate). The C1-position is the preferred one for the $^{13}$C isotopic enrichment. Further preferred samples are $^{13}$C-alanine, $^{13}$C-glycine, $^{13}$C-glutamine, $^{13}$C-glutamic acid, $^{13}$C-cysteine, $^{13}$C-asparagine, $^{13}$C-aspartic acid (all amino acids either in their protonated or deprotonated form), $^{13}$C-acetate, $^{13}$C-oxalate, $^{13}$C-malate, $^{13}$C-fumarate, $^{13}$C-lactate, $^{13}$C-lactic acid, $^{13}$C-citrate, $^{13}$C-bicarbonate, $^{13}$C-malonate, $^{13}$C-succinate, $^{13}$C-oxaloacetate, $^{13}$C-α-ketoglutarate, $^{13}$C-isocitrate, $^{13}$C-3-hydroxybutyrate and $^{13}$C-urea.

In another preferred embodiment, the sample of the method of the invention is used in solid state NMR spectroscopy. Here the hyperpolarised solid sample may be analysed by either static or magic angle spinning solid state NMR spectroscopy. In this embodiment, the sample is not limited to chemical compounds with certain properties and molecules of any size and type can be used as samples in this method.

The trityl radical used in the method of the invention works as a DNP agent, which is essential in the DNP method as the large electron spin polarisation of the DNP agent is converted to nuclear spin polarisation of nuclei within the sample via microwave irradiation close to electron Larmor frequency. The microwaves stimulate communication between electron and nuclear spin systems via e-e and e-n transitions. For effective DNP the DNP agent has to be stable and soluble in the sample to be polarised to achieve intimate contact between sample and DNP agent which is necessary for the aforementioned communication between electron and nuclear spin systems. In this context, stable trityl radicals proved to be highly useful DNP agents. Oxygen-based, sulphur-based or carbon-based stable trityl radicals are for instance described in WO-A-99/35508, WO-A-88/10419, WO-A-90/00904, WO-A-91/12024, WO-A-93/02711 or WO-A-96/39367.

The optimal choice of trityl radical depends on several aspects. As mentioned before, the trityl radical and the sample must be in intimate contact during DNP in order to result in optimal polarisation levels in the sample. Thus, in a preferred embodiment, the trityl radical is soluble in the sample or in a solution of the sample. To prepare such a solution of a sample, a solvent or a solvent mixture may be used to dissolve the sample. However if the polarised sample is used for in vivo applications like in vivo MR imaging it is preferred to keep the amount of solvent to a minimum or, if possible, to avoid the use of solvents. The latter might be possible if the sample to be polarised is for instance a liquid or if the sample is transferred into the liquid state, e.g. by melting it. To be used as an in vivo imaging agent, the polarised sample usually is administered in a relatively high concentration, i.e. a highly concentrated sample is preferably used in the DNP process and hence the amount of solvent is preferably kept to a minimum. In this context, it is also important to mention that the mass of the composition containing the sample (i.e. DNP agent, sample and if necessary solvent) is kept as small as possible. A high mass will have a negative impact on the efficiency of the dissolution process, if dissolution is used to convert the solid hyperpolarised sample after the DNP process into the liquid state, e.g. for using it as an MR imaging agent. It has been observed that the efficiency of the dissolution and thereby the preservation of the attained polarisation decreases as the mass of the composition increases. This is presumably due to the fact that the volume of the composition increases to the third whereas the surface of the composition increases to the second. Further, using certain solvents may require their removal before the hyperpolarised sample used as an MR imaging agent is administered to the patient since they might not be physiologically tolerable.

If the sample to be polarised is a lipophilic (hydrophilic) compound, the trityl radical should be lipophilic (hydrophilic) too. Lipophilicity or hydrophilicity of the trityl radical can be influenced by choosing suitable residues which render the trityl radical molecule lipophilic or hydrophilic. Further, the trityl radical has to be stable in presence of the sample. Hence if the sample to be polarised is an acid (a base), the trityl radical should be stable under acidic (basic) conditions. If the sample to be polarised contains reactive groups, a trityl radical should be used which is relatively inert towards these reactive groups. From the aforesaid it is apparent that the choice of trityl radical is highly dependent on the chemical nature of the sample.

J. H. Ardenkjær-Larsen et al, PNAS 100(18), 2003, 10158-10163 describe the successful DNP polarisation of $^{13}$C-labelled and unlabelled urea using the trityl radical (Tris{8-carboxyl-2,2,6,6-tetra[2-(1-hydroxyethyl)]-benzo(1,2-d:4,5-d')bis(1,3)dithiole-4-yl}methyl sodium salt (further described in U.S. Pat. No. 6,013,810) and glycerol as a solvent which resulted in high polarisation levels in urea.

In WO-A-2006/011811, trityl radicals are disclosed which are especially useful DNP agents for the DNP polarisation of acidic organic compounds like lactic acid or pyruvic acid.

In a preferred embodiment of the method according to the invention, the sample is pyruvic acid, more preferred $^{13}$C-pyruvic acid, most preferred $^{13}C_1$-pyruvic acid or pyruvate, more preferred $^{13}$C-pyruvate and most preferred $^{13}C_1$-pyruvate and the trityl radical is a radical of the formula (1)

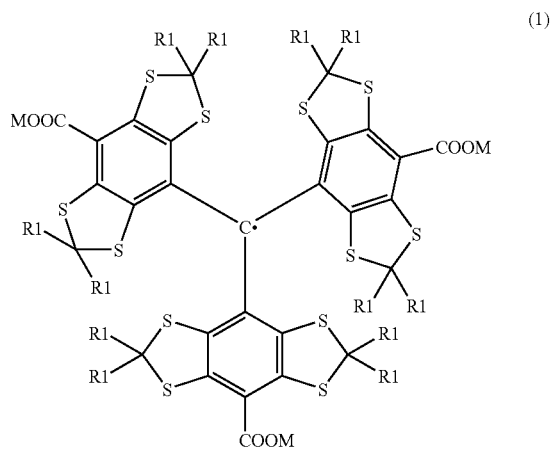

wherein
M represents hydrogen or one equivalent of a cation; and
R1 which is the same or different represents a straight chain or branched $C_1$-$C_6$-alkyl group or a group —$(CH_2)_n$—X—R2, wherein n is 1, 2 or 3;
X is O or S and R2 is a straight chain or branched $C_1$-$C_4$-alkyl group.

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, R1 is the same, more preferably a straight chain or branched $C_1$-$C_4$-alkyl group, most preferably methyl, ethyl or isopropyl.

In a further preferred embodiment, R1 is the same or different, preferably the same and represents —$CH_2$—$OCH_3$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, most preferably —$CH_2$—$CH_2$—$OCH_3$.

In a more preferred embodiment, M represents hydrogen or sodium and R1 is the same and represents —$CH_2$—$CH_2$—$OCH_3$.

The trityl radicals used in the method of the invention may be synthesized as described in detail in WO-A-88/10419, WO-A-90/00904, WO-A-91/12024, WO-A-93/02711, WO-A-96/39367 and WO-A-2006/011811.

The paramagnetic metal ion used in the method of the invention is a paramagnetic metal ion of a lanthanide metal of atomic numbers 58-70 or of a transition metal of atomic numbers 21-29, 42 or 44. Paramagnetic metal ions of one or different metals may be used in the method of the invention. Preferably, paramagnetic metal ions of one metal are used. Suitable paramagnetic ions include for instance $Cr^{3+}$, $Mn^{2+}$, $Fe^{3+}$, $Fe^{2+}$, $Co^{2+}$, $Ni^{2+}$, $Cu^{2+}$, $Nd^{3+}$, $Sm^{3+}$, $Gd^{3+}$, $Tb^{3+}$, $Dy^{3+}$, $Ho^{3+}$, $Er^{3+}$, and $Yb^{3+}$. In a preferred embodiment the paramagnetic metal ion is chosen from the group consisting of $Cr^{3+}$, $Mn^{2+}$, $Fe^{3+}$, $Fe^{2+}$, $Gd^{3+}$ and $Tb^{3+}$, in a more preferred embodiment from the group consisting of $Cr^{3+}$, $Mn^{2+}$, $Fe^{3+}$ and $Gd^{3+}$.

Suitably, paramagnetic metal ions are used in chelated form or in the form of their salts.

If the sample to be polarised is intended to undergo solid state NMR, paramagnetic metal ions are preferably used in form of their salts. Suitable salts are for example inorganic or organic salts of paramagnetic metal ions, e.g. $CrCl_3$, $MnCl_2$, $FeCl_2$, $FeCl_3$, $GdCl_3$, Gd(III) acetate or Gd(III) pyruvate. If the sample to be polarised is a liquid or a solution of the sample in a solvent it is of benefit to select a salt that is soluble in the liquid sample or the solution of the sample. In another embodiment, the paramagnetic metal ions may be added in chelated form.

For liquid state NMR or use as an imaging agent in a living human or animal body, the solid hyperpolarised sample has to be dissolved or melted to result in a solution or liquid. However free paramagnetic ions in such a solution or liquid dramatically shorten the $T_1$ relaxation time of the polarised nuclei in the sample, i.e. accelerating the natural decay of the polarisation and thus shortening the time the sample will provide MR signal intensities that are high enough to make the sample a useful MR imaging agent. On the other hand, free paramagnetic metal ions—if not removed from the final injectable imaging agent—often are not or poorly physiologically tolerated and may have unwanted effects, e.g. toxic effects.

To overcome the aforementioned effects of free paramagnetic metal ions, the paramagnetic metal ions may be used in chelated form. Alternatively, they may be used in form of their salts and rapidly removed after dissolving or melting the hyperpolarised sample. Methods for the rapid removal of free paramagnetic metal ions are discussed later in this application. In another embodiment, the aforementioned effects can be overcome by using paramagnetic metal ions in form of their salts and adding chelating agents to the dissolution medium to complex said free paramagnetic metal ions. In this case, a chelating agent should be chosen that is a) soluble and stable in the dissolution medium and b) rapidly forms a stable complex with the free paramagnetic metal ion.

As stated above, paramagnetic metal ions may be used in the method of the invention in chelated form. The term "paramagnetic chelate" hereinafter denotes paramagnetic metal ions in chelated form, i.e. complexes comprising paramagnetic metal ions and chelating agents.

A variety of chelating agents is known for this purpose. Generally, cyclic and acyclic chelating agents often containing heteroatoms like N, O, P or S may be used with cyclic chelating agents being the preferred ones. Suitable acyclic chelating agents are for instance DTPA and derivatives thereof like DTPA-BMA, DTPA-BP, DTPA-BMEA, EOB-DTPA, BOPTA and MS-325, EDTA and derivatives thereof like EDTA-BMA, DPDP, PLED, HPTA, amides or diamides like TOGDA, sulphonates or phosphonates. Suitable cyclic chelating agents are for instance cryptands, PCTA-[12], PCTP-[12], PCTP-[13], DOTA, DO3A and derivatives thereof like HP-DO3A and DO3A-butriol. DOTA, DO3A and derivatives thereof are preferred cyclic chelating agents. The aforementioned chelating agents are known in the art and so is their synthesis.

In another preferred embodiment, chelating agents are used that are relatively inert chemical entities like for instance fullerenes or zeolites. The use of such chelating agents (encapsulating a paramagnetic metal ion like $Gd^{3+}$) are preferred if the sample to be polarised is a reactive compound e.g. comprising reactive groups which would react with chelating agents comprising functional groups like those mentioned in the previous paragraph.

In the method of the invention, the paramagnetic chelates may either be monomeric paramagnetic chelates, i.e. chemical entities consisting of a chelating agent and a single paramagnetic metal ion like for instance GdDTPA-BMA or MnDPDP. On the other hand, the paramagnetic chelates may be multimeric paramagnetic chelates, i.e. chemical entities consisting of two or more subunits wherein each subunit consists of a chelating agent and a single paramagnetic metal ion. An example of a trimeric paramagnetic chelate is 1,3,5-tris-(N-(DO3A-acetamido)-N-methyl-4-amino-2-methylphenyl)-[1,3,5]triazinane-2,4,6-trione, a paramagnetic chelate consisting of a triazinetrione core with 3 subunits connected to said core wherein each subunit comprises $Gd^{3+}$ as the paramagnetic metal ion and a DO3A derivative as the chelating agent. The use of this trimeric paramagnetic chelate in the polarisation of pyruvic acid has resulted in high polarisation levels. The detailed synthesis of this trimeric paramagnetic chelate is described in the Example part of this application.

As with the trityl radical described before, the sample to be polarised must be in intimate contact with the paramagnetic metal ion. In the following, unless otherwise stated or specified, the term "paramagnetic metal ion" is used for both, paramagnetic metal ions, e.g. in form of their salts and paramagnetic chelates. If the sample is a liquid or a solution of the sample, it is preferred to use a paramagnetic metal ion which is soluble in the liquid sample or solution of the sample. If the sample to be polarised is a lipophilic (hydrophilic) compound and a paramagnetic chelate is used, the paramagnetic chelate should be lipophilic (hydrophilic) too. Lipophilicity or hydrophilicity of paramagnetic chelates can for instance be influenced by choosing chelating agents that comprise lipophilic or hydrophilic residues. Further, it is preferred that the paramagnetic chelate is stable in presence of the sample as complex dissociation (dechelation) will lead to free paramagnetic ions with detrimental consequences on the polarisation decay and hence polarisation level in a liquefied sample as described above, unless the free paramagnetic metal ions are rapidly and efficiently removed after the solid hyperpolarised sample has been liquefied or complexed by chelating agents in the dissolution medium. Further, if the sample to be polarised is an acid (a base), the paramagnetic metal ion should be stable under acidic (basic) conditions. If the sample to be polarised contains reactive groups, a paramagnetic metal ion should be used which is relatively inert towards these reactive groups. From the aforesaid it is apparent that the choice of the paramagnetic metal ion is highly dependent on the chemical nature of the sample and its final use (solid NMR, liquid NMR or imaging agent).

Another aspect of the invention is a method for producing a liquid hyperpolarised sample, the method comprising preparing a composition comprising the sample or a precursor thereof, a trityl radical and a paramagnetic metal ion, carrying out dynamic nuclear polarisation on the composition, liquefying the composition and optionally removing the trityl radical and/or the paramagnetic metal ion from the liquefied composition.

For carrying out the methods according to the invention, the first step is to prepare a composition comprising the sample, a trityl radical and a paramagnetic metal ion. If the sample used in the method of the invention is a liquid at room temperature, like for instance pyruvic acid, the sample is combined with the chosen trityl radical and the chosen paramagnetic metal ion to form a composition where the compounds are in intimate contact. Preferably, the chosen trityl radical and paramagnetic metal ion are soluble in the liquid sample. Intimate mixing can be further promoted by several means known in the art, such as stirring, vortexing or sonication. If the sample used in the method of the invention is a solid at room temperature, it may be melted and the melted sample is combined with the chosen trityl radical and the chosen paramagnetic metal ion. In another embodiment, a solution of the solid sample may be prepared, e.g. by dissolving the solid sample in an adequate solvent or solvent mixture, preferably in a solvent which is a good glass former and does prevent crystallization of the composition upon cooling/freezing. Suitable glass formers are for instance glycerol, propanediol or glycol. Subsequently, the dissolved sample is combined with the chosen trityl radical and the chosen paramagnetic metal ion. Glass formers may also be added to liquid samples or samples dissolved in non-glass forming solvents if the sample would crystallize upon cooling/freezing. However, as stated earlier, the addition of solvents and/or glass formers should be kept to the necessary minimum. Hence the preferred way is to select a trityl radical and a paramagnetic metal ion which are soluble in or miscible with the sample.

Suitably, the concentration of trityl radical is 5 to 25 mM, preferably 10 to 20 mM in the composition. Regarding the concentration of paramagnetic metal ion, 0.1 to 6 mM (metal ion) in the composition is suitable and a concentration of 0.5 to 4 mM is preferred.

The composition is cooled and/or frozen, preferably in such a way that crystallization is prohibited. Cooling/freezing may be achieved by methods known in the art, e.g. by freezing the composition in liquid nitrogen or by simply placing it in the DNP polariser, where liquid helium will freeze it.

The composition may be degassed before cooling/freezing. Degassing may be achieved by bubbling helium gas through the composition (e.g. for a time period of 2-15 min) but can be effected by other known common methods.

The DNP technique is for instance described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment, the DNP process is carried out in liquid helium and a magnetic field of about 1 T or above. Suitable polarisation units (=polarisers) are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region "P" near the superconducting magnet where the magnetic field strength is sufficiently high, e.g. between 1 and 25 T, for polarisation of the sample nuclei to take place. The bore for the probe (=composition to be polarised) is preferably sealable and can be evacuated to low pressures, e.g. pressures in the order of 1 mbar or less. A probe introducing means such as a removable transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The probe introducing means is preferably sealable at its upper end in any suitable way to retain the partial vacuum in the bore. A probe-retaining container, such as a probe-retaining cup, can be removably fitted inside the lower end of the probe introducing means. The probe-retaining container is preferably made of a lightweight material with a low specific heat capacity and good cryogenic properties such, e.g. KelF (polychlorotrifluoroethylene) or PEEK (polyetheretherketone) and it may be designed in such a way that it can hold more than one probe.

The probe is inserted into the probe-retaining container, submerged in the liquid helium and irradiated with microwaves, preferably at a frequency about 94 GHz at 200 mW. The level of polarisation may be monitored by for instance acquiring solid state NMR signals of the probe during microwave irradiation, depending on the sample to be polarised. Generally, a saturation curve is obtained in a graph showing NMR signal vs. time. Hence it is possible to determine when the optimal polarisation level is reached.

If the polarised sample is intended to be used as a MR imaging agent, the composition containing the hyperpolarised sample is preferably transferred from a solid state to a liquid state (i.e. liquefied), either by dissolving the solid composition after the DNP process in an appropriate solvent or solvent mixture, e.g. an aqueous carrier like a buffer solution or by melting it, optionally with a subsequent dissolution step or a dilution step in a suitable solvent or solvent mixture. Suitable methods and devices for the dissolution of a hypelpolarised solid composition are for instance described in WO-A-02/37132. Suitable methods and devices for the melting of a hyperpolarised solid composition are for instance described in WO-A-02/36005. If the hyperpolarised sample is intended to be used as a MR imaging agent, the solid composition containing the hyperpolarised sample is dissolved, preferably in an aqueous carrier or suitable solvent, to result in a physiologically tolerable solution. Alternatively, the solid composition containing the hyperpolarised sample is melted and the melted composition is diluted/dissolved, preferably in an aqueous carrier or suitable solvent, to result in a physiologically tolerable solution.

In context with the methods of the invention, the solvent used for the dissolution of the solid composition containing the hyperpolarised sample may also convert the hyperpolarised sample to a different hyperpolarised chemical entity. In this case, the solid hyperpolarised sample is denoted a "sample precursor". If for instance a solvent containing a base is used to dissolve a solid composition comprising a hyperpolarised acid (sample precursor), the hyperpolarised acid is neutralized and converted to a salt. Thus the liquid hyperpolarised sample would be a salt of the acid and no longer the acid itself.

In a subsequent step of the method according to the invention the trityl radical and/or the paramagnetic metal ion and/or reaction products thereof are optionally removed from the liquefied composition. If the hyperpolarised sample is intended to be used as a MR imaging agent in a living human or animal being, both the trityl radical and the paramagnetic metal ion are preferably removed from the liquefied composition.

Methods useful to partially, substantially or completely remove the trityl radical and the paramagnetic metal ion are known in the art. Generally, the methods applicable depend on the nature of the trityl radical and the paramagnetic metal ion. Upon dissolution or melting of the solid composition containing the hyperpolarised sample, the trityl radical and/or the paramagnetic metal ion might precipitate and thus may easily be separated from the liquid by filtration. Whether precipitation occurs or not is of course dependent on the nature of the solvent and the nature of the trityl radical and/or the paramagnetic metal ion.

If no precipitation occurs, the trityl radical and the paramagnetic metal ion may be removed by chromatographic separation techniques, e.g. liquid phase chromatography like reversed phase, ion exchange chromatography, (solid phase) extraction or other chromatographic separation methods known in the alt. In general, it is preferred to use a method which is able to remove both the trityl radical and the paramagnetic metal ion in one step as polarisation in the liquid sample decays due to $T_1$ relaxation. The faster any unwanted compounds are removed from the liquid sample the higher the polarisation level retained in the sample. Hence not only from the point of having an intimate contact between sample, trityl radical and paramagnetic metal ion but also from the point of a fast and efficient removal it is of benefit to select a trityl radical and a paramagnetic metal ion which have similar chemical properties, e.g. are both lipophilic or hydrophilic chemical compounds. If for instance a lipophilic trityl radical and a lipophilic paramagnetic chelate are used, both compounds could be removed in one step by reversed phase liquid chromatography on a single chromatography column.

If free paramagnetic metal ions are present in the liquefied composition (e.g. due to the use of a paramagnetic metal salt), these ions are preferably removed by using a cation exchange column or ionic imprinted resins as disclosed by O. Vigneau et al., Anal. Chim. Acta 435(1), 2001, 75-82. Another possible method is nano-filtration by selective complexation of free paramagnetic metal ions onto a charged organic membrane, as disclosed by A. Sorin et al., J. Membrane Science 267(1-2), 2005, 41-49. Further, free paramagnetic metal ions may be removed from the liquefied composition by affinity chromatography in analogy to what is disclosed by S. Donald et al. J. Inorg. Biochem. 56(3), 1994, 167-171. In another embodiment, free paramagnetic metal ions may be removed by surface modified polymer extraction, Smopex®. The Smopex® scavengers contain active scavenging groups that are almost exclusively located on the surface of fibres. The show fast reaction kinetics, high metal loading and are mechanical and chemical stable. In yet another embodiment, free paramagnetic metal ions may be removed by precipitation, either by choosing a dissolution medium which forms a compound of low solubility with the free paramagnetic metal ion, e.g. a salt of low solubility or by adding a precipitation aid to the composition before the composition is polarised. If for instance the composition comprises a $Gd^{3+}$-salt like $GdCl_3$, $Na_3PO_4$ could be added as a precipitation aid to the composition and the composition thus comprising the sample, the trityl radical, $GdCl_3$ and $Na_3PO_4$ undergoes dynamic nuclear polarisation. Upon dissolution in for instance an aqueous carrier, $GdCl_3$ and $Na_3PO_4$ will form a Gd-phosphate of low solubility which precipitates and thus may be easy to remove by filtration. On the other hand, a solid composition comprising the hyperpolarised sample, the trityl radical and $GdCl_3$ may be dissolved in an aqueous carrier containing $Na_3PO_4$ to form a Gd-phosphate of low solubility which precipitates.

As trityl radicals have a characteristic UV/visible absorption spectrum, it is possible to use UV/visible absorption measurement as a method to check for their presence in the liquid sample after their removal. In order to obtain quantitative results, i.e. the concentration of the trityl radical present in the liquid sample, the optical spectrometer can be calibrated such that absorption at a specific wavelength from an aliquot of the liquid sample yields the corresponding trityl radical concentration in the sample. Removal of the trityl radical is especially preferred if the liquid hyperpolarised sample is used as an imaging agent for in vivo MR imaging of a human or non-human animal body.

After removal of the paramagnetic metal ion and/or the trityl radical, the liquid sample may be checked for residual paramagnetic metal ion and/or trityl radical.

Fluorescence or UV/visible absorption measurement can be used as a method to check for the presence of paramagnetic chelates, provided that the chelates contain a (strong) chromophore. Another way to check for the presence of paramagnetic chelates is electrochemical detection, provided an electroactive moiety exists in the chelate.

If paramagnetic metal salts were used in the composition, fluorescence measurements may be used to check for free paramagnetic metal ions after their removal from the liquid composition. If for instance a $Gd^{3+}$-salt is used, fluorescence with an excitation wavelength of 275 nm and monitoring of emission at 314 nm may be used as a method to detect free $Gd^{3+}$ with high specificity. Further, free $Gd^{3+}$ can be detected by visible absorbance at 530-550 nm following complexation with the colorimetric agent PAR (4-(2-pyridylazo)resorcinol). Other colorimetric agents for other paramagnetic metal ions are known in the art and can be used in the same way.

In a preferred embodiment of the method according to the invention the composition comprises $^{13}C$-pyruvic acid, preferably $^{13}C_1$-pyruvic acid as a sample precursor or $^{13}C$-pyruvate, preferably $^{13}C_1$-pyruvate as a sample, a trityl radical of formula (1) and a paramagnetic metal ion which is either a paramagnetic chelate comprising $Gd^{3+}$ or a $Gd^{3+}$-salt like $GdCl_3$ or Gd(III) pyruvate. A composition is prepared by dissolving the trityl radical of formula (1) and the paramagnetic metal ion in $^{13}C$-pyruvic acid or in a solution of $^{13}C$-pyruvate in a solvent, preferably water and optionally a glass former. The compounds are thoroughly mixed and the composition is cooled and/or frozen. After dynamic nuclear polarisation, the solid composition comprising the hyperpolarised $^{13}C$-pyruvic acid or $^{13}C$-pyruvate is either dissolved in an aqueous carrier, preferably an aqueous buffer solution or melted and subsequently dissolved/diluted with an aqueous carrier.

In the case of $^{13}C$-pyruvic acid (sample precursor) the composition is neutralised with a base to yield $^{13}C$-pyruvate (sample). In one embodiment, the solid composition containing hyperpolarised $^{13}C$-pyruvic acid is reacted with a liquid base to simultaneously dissolve and convert it to $^{13}C$-pyruvate and subsequently a buffer solution is added to finalise dissolution and optionally convert residual $^{13}C$-pyruvic acid to $^{13}C$-pyruvate. In a preferred embodiment, the base is an aqueous solution of NaOH. In a further preferred embodiment, the buffer solution is a TRIS buffer solution, a citrate buffer solution or a phosphate buffer solution. In another preferred embodiment the buffer solution and the base are combined in one alkaline solution and this solution is added to the solid composition containing the hyperpolarised $^{13}C$-pyruvic acid, dissolving and converting the $^{13}C$-pyruvic acid into $^{13}C$-pyruvate at the same time.

If a $Gd^{3+}$-salt has been used as paramagnetic metal ion it is important to remove $Gd^{3+}$ ions from the dissolved $^{13}C$-pyruvate as quickly and efficiently as possible. Suitable methods are the removal by using a cation exchange column or ionic imprinted resins as disclosed by O. Vigneau et al., Anal. Chim. Acta 435(1), 2001, 75-82. Another possible method is nano-filtration by selective complexation of free $Gd^{3+}$ onto a charged organic membrane, as disclosed by A. Sorin et al., J. Membrane Science 267(1-2), 2005, 41-49. Further, free $Gd^{3+}$ may be removed by affinity chromatography as disclosed by S. Donald et al. J. Inorg. Biochem. 56(3), 1994, 167-171. In a further preferred embodiment, free $Gd^{3+}$ is removed by adding chelating agents to the dissolution medium that are able to quickly and efficiently complex said free $Gd^{3+}$, for instance chelating agents like DTPA, DTPA-BMA, EDTA or derivatives of EDTA and DTPA. The so obtained Gd-chelates may be removed from the dissolved sample as described in the next paragraph.

If a Gd-chelate has been used as paramagnetic metal ion, the chelate may be removed by using reversed phase liquid chromatography, which would allow for the simultaneous removal of the trityl radical of formula (1) and the Gd-chelate.

Suitable methods to check for residual free $Gd^{3+}$, Gd-chelate and trityl radical of formula (1) in the purified liquid sample are described on page 18/19.

If the composition comprises $^{13}C$-pyruvic acid, a trityl radical of formula (1) and a $Gd^{3+}$-salt and the solid composition is melted, free $Gd^{3+}$ metal ions are preferably removed before the hyperpolarised $^{13}C$-pyruvic acid comprised in the melted composition is neutralised with a base to yield $^{13}C$-pyruvate. The conversion to $^{13}C$-pyruvate and dissolution/dilution may be carried out as described before. The removal of free $Gd^{3+}$ metal ions from the melted composition is preferably carried out by cation exchange solid phase extraction, e.g. by using suitable cation exchange solid phase extraction cartridges or columns.

Liquid hyperpolarised $^{13}C$-pyruvate produced according to the method of the invention may be used as a "conventional" MR imaging agent, i.e. providing contrast enhancement for anatomical imaging. A further advantage of liquid hyperpolarised $^{13}C$-pyruvate produced according to the method of the invention is that pyruvate is an endogenous compound which is very well tolerated by the human body, even in high concentrations. As a precursor in the citric acid cycle, pyruvate plays an important metabolic role in the human body. Pyruvate is converted into different compounds: its transamination results in alanine, via oxidative decarboxylation, pyruvate is converted into acetyl-CoA and bicarbonate, the reduction of pyruvate results in lactate and its carboxylation in oxaloacetate.

Further, the metabolic conversion of hyperpolarised $^{13}C$-pyruvate to hyperpolarised $^{13}C$-lactate, hyperpolarised $^{13}C$-bicarbonate (in the case of $^{13}C_1$-pyruvate, $^{13}C_{1,2}$-pyruvate or $^{13}C_{1,2,3}$-pyruvate only) and hyperpolarised $^{13}C$-alanine can be used for in vivo MR studying of metabolic processes in the human body. $^{13}C$-pyruvate has a $T_1$ relaxation in human full blood at 37° C. of about 42 s, however, the conversion of hyper-polarised $^{13}C$-pyruvate to hyperpolarised $^{13}C$-lactate, hyperpolarised $^{13}C$-bicarbonate and hyperpolarised $^{13}C$-alanine has been found to be fast enough to allow signal detection from the $^{13}C$-pyruvate parent compound and its metabolites. The amount of alanine, bicarbonate and lactate is dependent on the metabolic status of the tissue under investigation. The MR signal intensity of hyperpolarised $^{13}C$-lactate, hyperpolarised $^{13}C$-bicarbonate and hyperpolarised $^{13}C$-alanine is related to the amount of these compounds and the degree of polarisation left at the time of detection, hence by monitoring the conversion of hyperpolarised $^{13}C$-pyruvate to hyperpolarised $^{13}C$-lactate, hyperpolarised $^{13}C$-bicarbonate and hyperpolarised $^{13}C$-alanine it is possible to study metabolic processes in vivo in the human or non-human animal body by using non-invasive MR imaging.

It has been found that the MR signal amplitudes arising from the different pyruvate metabolites vary depending on the tissue type. The unique metabolic peak pattern formed by alanine, lactate, bicarbonate and pyruvate can be used as fingerprint for the metabolic state of the tissue under examination and thus allows for the discrimination between healthy tissue and tumour tissue. This makes the composition according to the invention an excellent agent for in vivo MR tumour imaging. The use of hyperpolarised $^{13}C$-pyruvate for tumour imaging has been described in detail in WO-A-2006/011810.

Further, the use of hyperpolarised $^{13}C$-pyruvate for cardiac imaging has been described in WO-A-2006/054903.

Another aspect of the invention is a composition comprising a sample, a trityl radical and a paramagnetic metal ion.

Yet another aspect of the invention is a composition comprising a sample, a trityl radical and a paramagnetic metal ion for use in a dynamic nuclear polarisation.

Yet another aspect of the invention is a composition comprising a hyperpolarised sample, a trityl radical and a paramagnetic metal ion, the composition being obtained by dynamic nuclear polarisation.

Yet another aspect of the invention is a polarising agent for use in dynamic nuclear polarisation wherein the polarising agent comprises a trityl radical and a paramagnetic metal ion. In a preferred embodiment, the polarising agent consists of a trityl radical and a paramagnetic metal ion, more preferably of a trityl radical and a paramagnetic chelate or a trityl radical and a paramagnetic metal ion in form of its salt.

EXAMPLES

Example 1

Comparison of Solid State Polarisation of $^{13}C_1$-Pyruvic Acid with and without GdDTPA-BMA as a Paramagnetic Chelate

Example 1a

Synthesis of the Trityl Radical tris(8-carboxy-2,2,6, 6-(tetra(methoxyethyl)benzo-[1,2-4,5']bis-(1,3)dithiole-4-yl)methyl Sodium Salt 10 g (70 mmol) tris-(8-carboxy-2,2,6,6-(tetra(hydroxyethyl)benzo-[1,2-4,5']-bis-(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 1b

Production of Hyperpolarised $^{13}C_1$-Pyruvic Acid Using the Radical of Example 1a A composition being 15 mM in trityl radical of Example 1a was prepared by dissolving the trityl radical of Example 1a) in a mixture of $^{13}C_1$-pyruvic acid (553 mg) and unlabelled pyruvic acid (10.505 g). The composition was mixed to homogeneity and an aliquot of the solution (2.015 g) was placed in a probe cup and inserted in the DNP polariser. The composition was polarised under DNP conditions at 1.2 K in a 3.35 T magnetic field under irradiation with microwave (93.950 GHz). After 4 hours the polarisation was stopped.

The solid state polarisation was determined by solid state $^{13}C$-NMR to be 5.72 (integral) per mg solid composition. The solid state $^{13}C$-NMR measurement consisted of a simple pulse-acquire NMR sequence using a low flip angle. The signal intensity of the dynamic nuclear polarised sample is compared with the thermally polarised sample, i.e. the natural polarisation of the sample at room temperature before the start of the dynamic nuclear polarisation process. To determine when the sample has reached its maximum polarisation, low flip angle solid $^{13}C$-NMR spectra were acquired at different time points after starting the dynamic nuclear polarisation process. The polarisation was calculated from the ratio of the signal intensities of the thermally polarised sample and the dynamic nuclear polarised sample.

Example 1c

Production of Hyperpolarised $^{13}C_1$-Pyruvic Acid Using the Radical of Example 1a) and GdDTPA-BMA The example was carried out according to Example 1b apart from that the composition contained GdDTPA-BMA, which was dissolved together with the trityl radical in the mixture of $^{13}C_1$-pyruvic acid and unlabelled pyruvic acid. The composition was 15 mM in radical and 1.5 mM in $Gd^{3+}$. The composition was polarised under DNP conditions at 1.2 K in a 3.35 T magnetic field under irradiation with microwave (93.950 GHz). After 4 hours the polarisation was stopped.

The solid state polarisation was determined by solid state $^{13}C$-NMR carried out as described in Example 1b to be 9.69 (integral) per mg solid composition.

Due to the presence of a paramagnetic metal ion in the composition to be polarised the solid state polarisation of $^{13}C$-pyruvic acid could almost be doubled.

Example 2

Comparison of Solid State Polarisation of $^{13}C_1$-Pyruvic Acid with and without Gd(III) Acetate A composition being 15 mM in trityl radical was prepared by dissolving the trityl radical of Example 1a in 43.7 mg of $^{13}C_1$-pyruvic acid. The composition was mixed to homogeneity, placed in a probe cup and inserted in the DNP polariser. The composition was polarised under DNP conditions at 1.2 K in a 3.35 T magnetic field under irradiation with microwave (93.950 GHz).

The solid state polarisation was determined by solid state $^{13}C$-NMR carried out as described in Example 1b to be 5.72 (integral) per mg solid composition.

In another experiment, a composition being 15 mM in trityl radical was prepared by dissolving the trityl radical of Example 1a) in 43.7 mg of $^{13}C_1$-pyruvic acid. Further, Gd(III) acetate was added to the mixture to result in a composition being 2 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz).

The solid state polarisation was determined by solid state $^{13}$C-NMR carried out as described in Example 1b to be 9.37 (integral) per mg solid composition.

The addition of a paramagnetic metal ion resulted in a solid state polarisation enhancement of about factor 2.

Example 3

Production of a Solution of Hyperpolarised $^{13}$C$_1$-Pyruvate without the Presence of a Paramagnetic Metal Ion (Comparison Example)

43 mg of a composition being 18.9 mM in trityl radical was prepared by dissolving the trityl radical of Example 1a in $^{13}$C$_1$-pyruvic acid. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped and the composition was dissolved using a dissolution device according to WO-A-02/37132 in an aqueous solution of sodium hydroxide and tris(hydroxymethyl)aminomethane (TRIS) to provide a neutral solution of hyperpolarised sodium $^{13}$C$_1$-pyruvate with a total pyruvate concentration of approximately 78 mM in 40 mM TRIS buffer.

Liquid state polarisation was determined by liquid state $^{13}$C-NMR at 400 MHz to be 20.8%.

Example 4

Synthesis of the Gd-chelate of 1,3,5-Tris-(N-(DO3A-acetamido)-N-methyl-4-amino-2-methyl-phenyl)-[1,3,5]triazinane-2,4,6-trione (10)

4a) Preparation of 2-Methyl-4-nitrophenylisocyanate (1)

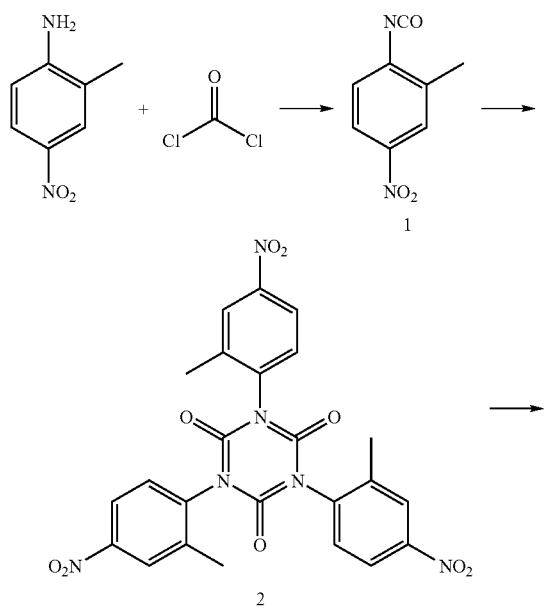

-continued

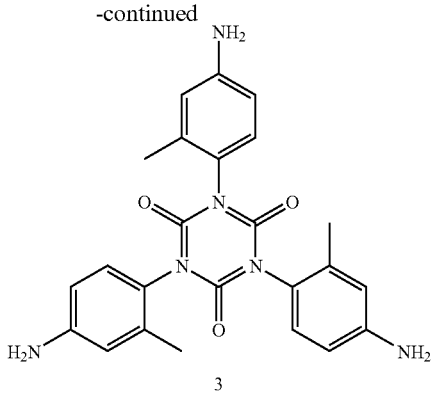

2-Methyl-4-nitroaniline (35.0 g, 230 mmol) was dissolved in ethyl acetate (400 ml) and cooled to 0° C. Phosgene (180 ml, 20% in toluene) was added drop wise over 30 min, precipitation of a white salt followed instantly. After the last addition the temperature was allowed to slowly rise to room temperature, and then the reaction mixture was brought to reflux (~100° C.). It was refluxed for 2 h 30 min, after which 200 ml of solvent was distilled off before the temperature was lowered to 80° C. and phosgene (140 ml, 20% in toluene) was added drop wise. After the last addition the reaction solution was refluxed for 3 hours, allowed to cool to room temperature and concentrated to dryness. The brown/yellow material was dissolved in diethyl ether (250 ml), filtered and concentrated to give a pale brown powder (36 g, 88%).

4b) Preparation of 1,3,5-Tris-(4-nitro-2-methyl-phenyl)-[1,3,5]triazinane-2,4,6-trione (2)

To 2-methyl-4-nitrophenylisocyanate (36.0 g) in a 250 ml flask was added DMSO (50 ml) and the flask was sealed with a glass stopper which was kept in place with a plastic clip. The flask was immediately lowered into an oil bath heated to 85° C. and the dark brown reaction solution was heated for 16 h 30 min. The oil bath was removed and the reaction solution was allowed to cool to room temperature before being poured into water (800 ml), sonicated, and the precipitate was filtered off. The filter cake was added to ethanol (500 ml) and was refluxed for 4 hours, then allowed to cool to room temperature and the product was filtered off to give an off-white powder (28.1 g, 78%).

4c) Preparation of 1,3,5-Tris-(4-amino-2-methyl-phenyl)-[1,3,5]triazinane-2,4,6-trione (3)

1,3,5-tris-(4-nitro-2-methyl-phenyl)-[1,3,5]triazinane-2,4,6-trione (2.86 g, 5.4 mmol) was dissolved in THF (70 ml). HCl (4.5 ml, 6M), water (18 ml) and Pd/C (0.6 g, 10%) was added. The reaction vessel was evacuated and filled with argon in three cycles before hydrogenated on a Parr hydrogenation apparatus (60 psi). After 2 hours the excess hydrogen was evacuated with a membrane pump and the Pd/C (10%) was filtered off. The clear reaction solution was concentrated until no more THF remained and the pH adjusted to 7 with NaHCO$_3$ (~3.7 g). The aqueous phase was extracted with ethyl acetate (3×100 ml) and the combined organic phases were dried with MgSO$_4$, filtered and concentrated to give a brown powder. The crude product was recrystallized from methanol to give the product as an off-white powder (1.9 g, 80%).

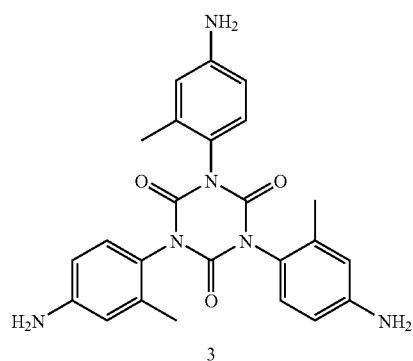

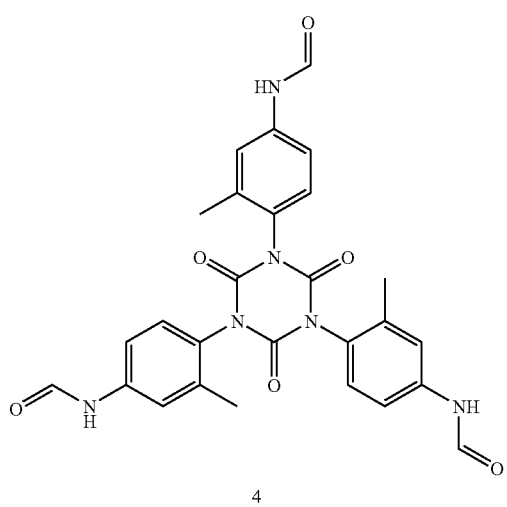

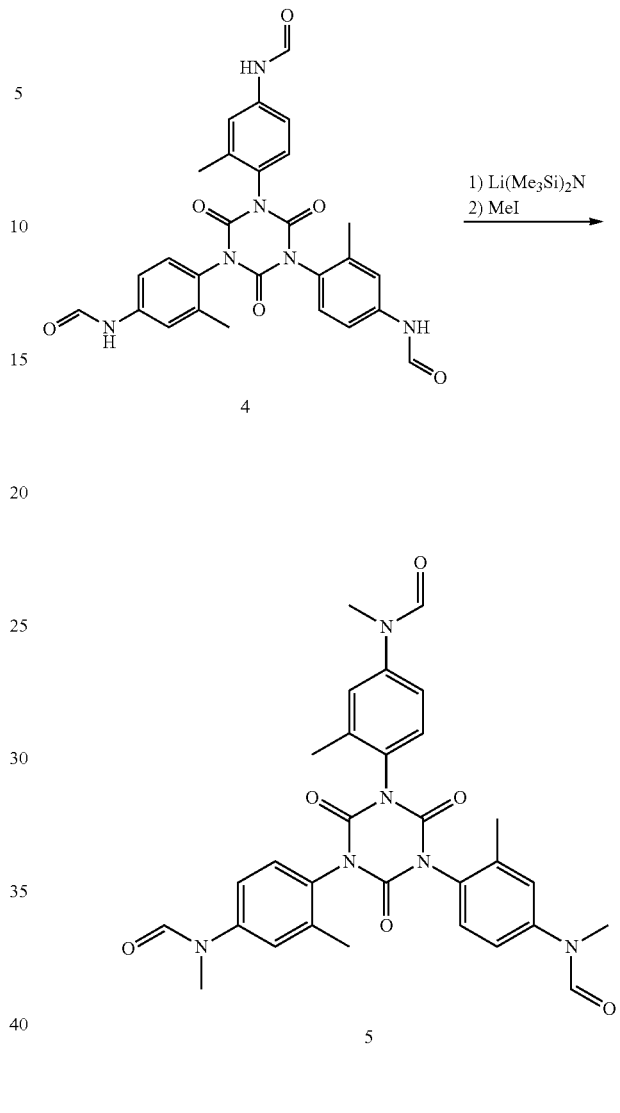

4d) Preparation of 1,3,5-Tris-(4-formamido-2-methyl-phenyl)-[1,3,5]triazinane-2,4,6-trione (4)

Formic acid (175 ml) was put in an ice-cooled 500 ml round-bottom flask. Acetic anhydride (15 ml, 0.16 mol) was added and the yellow solution was stirred under argon for 1 h at 0° C. The triamine 3 (8.7 g, 0.020 mol) was added to this solution and the ice bath was removed. After stirring under argon at room temperature for 30 minutes HPLC showed complete reaction. The solvent was removed in vacuo and the brown, sticky residue was suspended in $H_2O$ and filtered off. It was then washed thoroughly with $H_2O$ to make sure all acid was removed. The product was a pale-brown solid (10.2 g, 99%).

4e) Preparation of 1,3,5-Tris-(N-formyl-N-methyl-4-amino-2-methyl-phenyl)-[1,3,5]triazinane-2,4,6-trione (5)

All glassware was carefully dried in oven and DMF was dried over 4 Å molecular sieves. Li(Me$_3$Si)$_2$N (116 ml, 0.116 mol, 1 M in hexane) was added to a DMF-solution (115 ml) of 4 (10.2 g, 0.0193 mol) in 500 ml round-bottom flask. The reaction mixture, which turned from a light brown solution to a brick-red slurry, was stirred under argon for 1 h. Methyl iodide (12.2 ml, 0.196 mol) was added and the reaction mixture was stirred for 2 h or until complete methylation could be shown on HPLC. The hexane was then removed on rotary evaporator and the residue was poured into a solution of NaH$_2$PO$_4$ (1300 ml, 100 mM) under vigorous stirring. The precipitate of 5 formed was filtered off as a pale solid (6.7 g, 60%).

21

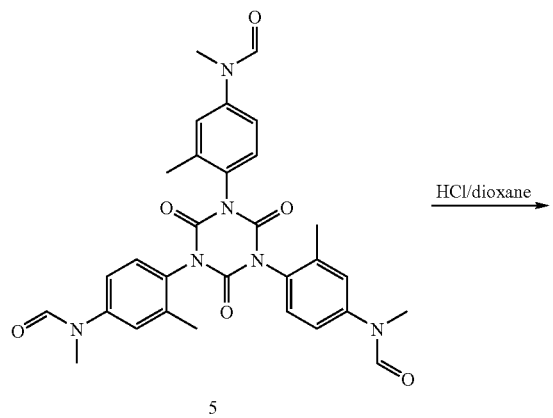

5

HCl/dioxane →

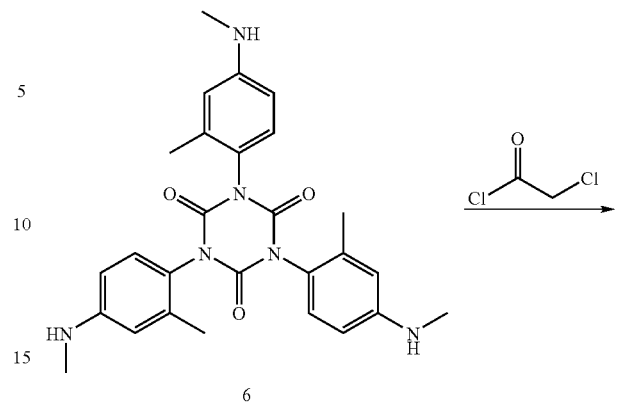

6

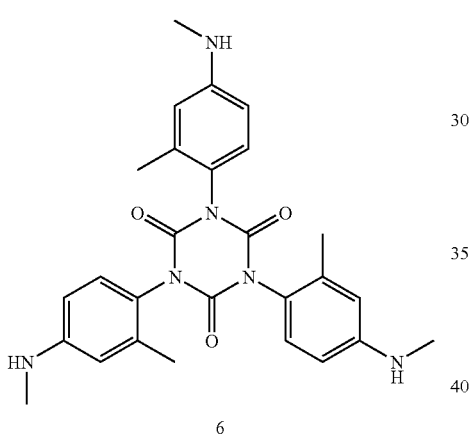

6

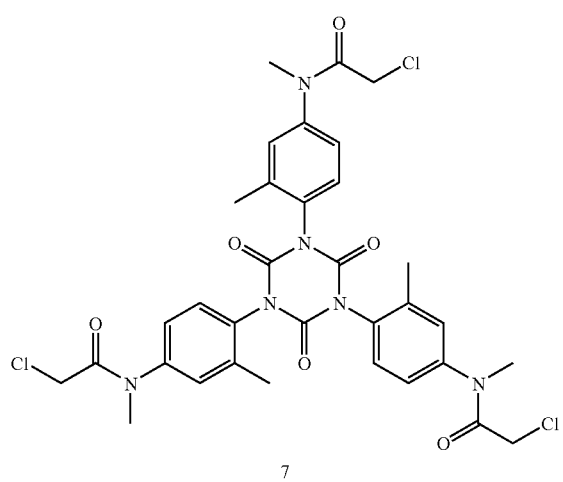

7

4f) Preparation of 1,3,5-Tris-(N-methyl-4-amino-2-methyl-phenyl)-[1,3,5]triazinane-2,4,6-trione (6)

4g) Preparation of 1,3,5-Tris-(N-chloroacetyl-N-methyl-4-amino-2-methyl-phenyl)-[1,3,5]triazinane-2,4,6-trione (7)

Dioxane (52 ml), HCl (52 ml, 6 M) and 5 (6.5 g, 11 mmol) were mixed in a 250 ml round-bottom flask to form a pale slurry. The reaction mixture was heated to reflux for 30 minutes under argon. The now yellow solution was allowed to cool to room temperature and solvents were then removed on a rotary evaporator. The orange residue was then dissolved in 500 ml $H_2O$ and neutralized with a solution of $NaHCO_3$ (sat.) under vigorous stirring. The precipitate formed was filtered off and washed several times with $H_2O$ giving a pale solid (4.7 g, 84%).

In a 100 ml round-bottom flask 6 (4.6 g, 9.5 mmol) was dissolved in DMA (15 ml) and chloroacetyl chloride (2.6 ml, 33 mmol) was added under stirring at 0° C. The reaction was stirred under argon at RT for 30 min or until HPLC showed complete chloroacetylation. The slurry was then poured into a large beaker with water (500 ml) under vigorous mechanical stirring. The precipitate formed was filtered off and dried in vacuo at 0.3 mbar (6.3 g). The pale solid was dissolved in 70 ml acetonitrile and poured into 500 ml $H_2O$ under vigorous mechanical stirring. The precipitate formed was filtered off and left to dry in a desiccator (6.1 g, 89%).

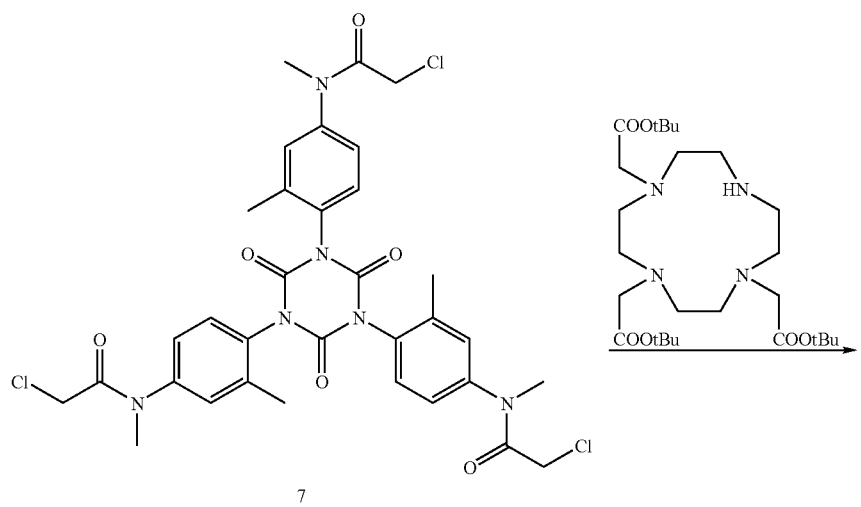

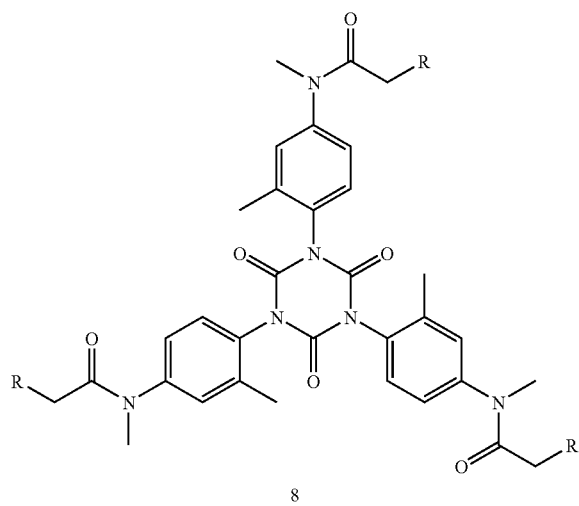

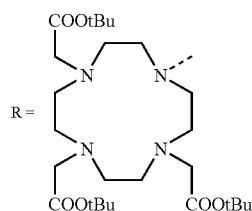

4h) Preparation of 1,3,5-Tris-(N-(DO3A t-butylester-acetamido)-N-methyl-4-amino-2-methyl-phenyl)-[1,3,5]triazinane-2,4,6-trione (8)

In a 50 ml round-bottom flask, 7 (0.50 g, 0.70 mmol) was suspended together with DO3A t-butyl ester (2.5 g, 4.2 mmol), diisopropylethylamine (910 µl, 5.2 mmol) and acetonitrile (15 ml). After sonication the reaction mixture was stirred at 75° C. under argon until LC/MS showed complete coupling. The solvents were then removed on rotary evaporator and the crude product (2.9 g) was used in the subsequent reaction.

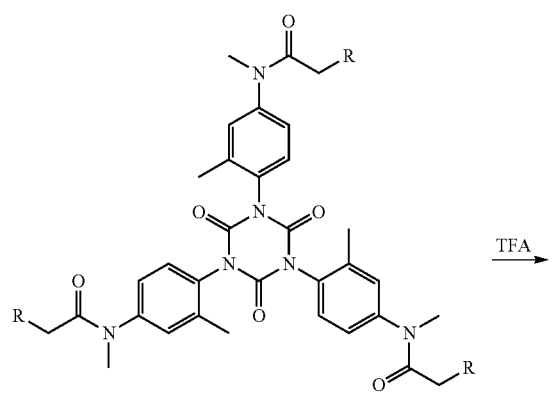

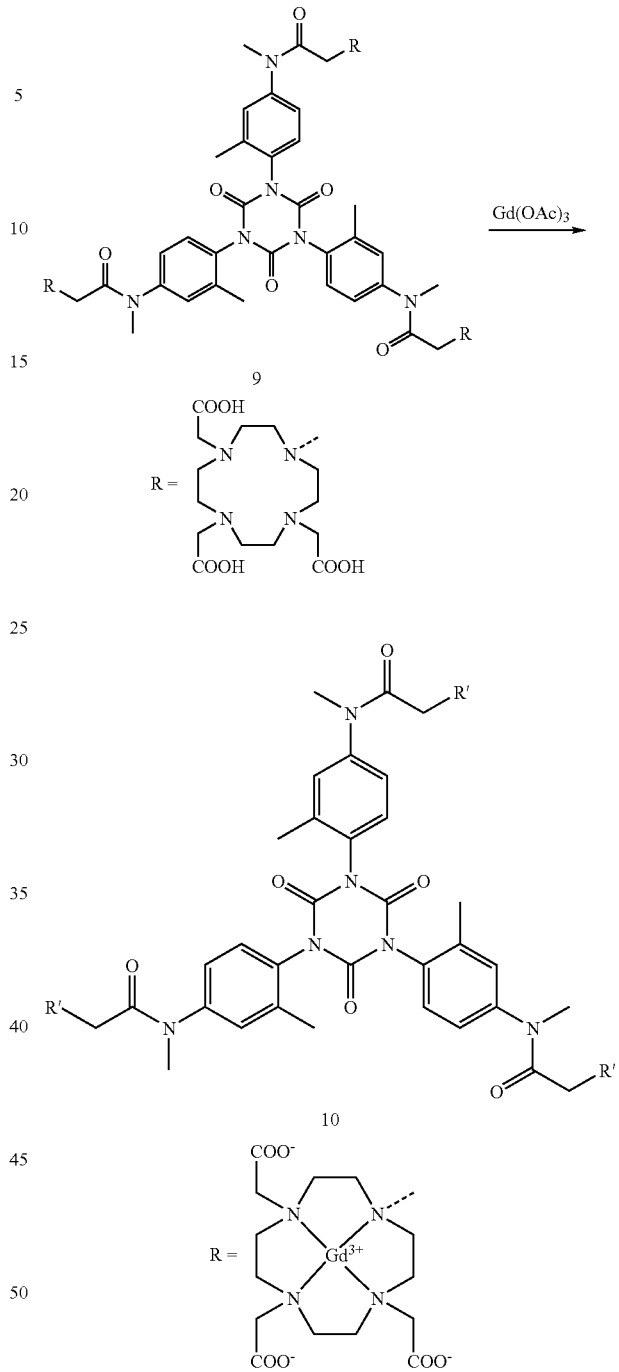

4i) Preparation of 1,3,5-Tris-(N-(DO3A-acetamido)-N-methyl-4-amino-2-methyl-phenyl)-[1,3,5]triazinane-2,4,6-trione (9)

The crude product of 8 (1.9 g) was dissolved in TFA (130 ml) and CH$_2$Cl$_2$ (130 ml) and was stirred at 50° C. under argon. The solution was stirred for 1 h or until LC/MS showed complete deprotection. The solvents were then removed on rotary evaporator and the residue was dried in vacuo overnight. The crude product (2.4 g) was then used in the final step.

4j) Preparation of Gadolinium Chelate of 1,3,5-Tris-(N-(DO3A-acetamido)-N-methyl-4-amino-2-methyl-phenyl)-[1,3,5]triazinane-2,4,6-trione (10)

The crude product of 9 (2.4 g) was dissolved in water and Gd(OAc)$_3$ (1.4 g, 4.2 mmol) was added under stirring. Vacuum (0.3 mbar) was then put on and the reaction was monitored continuously by LC/MS. When complete complexation was detected, the solvents were removed in vacuo. The crude product of 3.1 g was then purified by preparative HPLC (410 mg, 42% from 7)

Example 5

Production of a Solution of Hyperpolarised $^{13}C_1$-Pyruvate in the Presence of the Gd-Chelate of Example 4

43 mg of a composition being 18.9 mM in trityl radical was prepared by dissolving the trityl radical of Example 1a in $^{13}C_1$-pyruvic acid. The Gd-chelate of Example 4 was added to result in a composition being 0.63 mM in Gd-chelate of Example 4, i.e. 1.89 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped and the composition was dissolved using a dissolution device according to WO-A-02/37132 in an aqueous solution of sodium hydroxide and TRIS to provide a neutral solution of hyperpolarised sodium $^{13}C_1$-pyruvate with a total pyruvate concentration of approximately 78 mM in 40 mM TRIS buffer.

Liquid state polarisation was determined by liquid state $^{13}C$-NMR at 400 MHz to be 44.7%.

The comparison of Example 3 and Example 5 shows that due to the presence of a paramagnetic metal ion in the composition the polarisation level in the sample could be enhance by more than a factor 2.

Example 6

Production of a Solution of Hyperpolarised $^{13}C_1$-Pyruvate in the Presence of a Paramagnetic Metal Ion and Degassing the Composition Before Polarisation 43 mg of a composition being 15 mM in trityl radical was prepared by dissolving the trityl radical of Example 1a in $^{13}C_1$-pyruvic acid. The Gd-chelate of Example 4 was added to result in a composition being 0.5 mM in Gd-chelate of Example 4, i.e. 1.5 mM in $Gd^{3+}$. The composition was degassed by being bubbled with helium gas for 10 min in order to remove air. The composition was hereby concentrated with respect to the trityl radical and the Gd-chelate resulting in a composition being 18.9 mM in trityl radical of Example 1a) and 0.63 mM in Gd-chelate of Example 4, i.e. 1.89 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped and the composition was dissolved using a dissolution device according to WO-A-02/37132 in an aqueous solution of sodium hydroxide and TRIS to provide a neutral solution of hyperpolarised sodium $^{13}C_1$-pyruvate with a total pyruvate concentration of approximately 78 mM in 40 mM TRIS buffer.

Liquid state polarisation was determined by liquid state $^{13}C$-NMR at 400 MHz to be 55.3%.

The comparison of Example 5 and Example 6 shows that by degassing the composition the polarisation level in $^{13}C_1$-pyruvate could be even further enhanced by about 10%.

Example 8

Comparison of the Solid State Polarisation of 1,1-bis(hydroxy-methyl)cyclopropane-1-$^{13}C$ with and without the Gd-Chelate of Example 4

A composition being 15 mM in trityl radical was prepared by dissolving the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in a mixture of 9 µl of 1,1-bis(hydroxymethyl)cyclopropane-1-$^{13}C$ and 36 µl ethylene glycol. The composition was mixed to homogeneity, placed in a composition cup and inserted in the DNP polariser. The composition was polarised under DNP conditions at 1.2 K in a 3.35 T magnetic field under irradiation with microwave (93.950 GHz). After 3 hours the polarisation was stopped.

The solid state polarisation was determined by solid state $^{13}C$-NMR carried out as described in Example 1b to be 25.8 (integral).

In another experiment, a composition being 15 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in 9 µl of 1,1-bis(hydroxymethyl)cyclopropane-1-$^{13}C$ and 36 µl ethylene glycol. Further, the Gd-chelate of Example 4 was added to result in a composition being 0.62 mM in the Gd-chelate of Example 4, i.e. 1.86 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 3 hours the polarisation was stopped.

The solid state polarisation was determined by solid state $^{13}C$-NMR as described in Example 1b to be 44.9 (integral).

The addition of a paramagnetic metal ion resulted in a solid state polarisation enhancement of about factor 2.

Example 9

Comparison of the Solid State Polarisation of $^{13}C_1$-Pyruvic Acid with and without $GdCl_3$ A composition being 15 mM in trityl radical was prepared by dissolving 3.1 mg of the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in 90 µl $^{13}C_1$-pyruvic acid. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped.

The solid state polarisation was determined by solid state $^{13}C$-NMR as described in Example 1b to be 25%.

In another experiment, a composition being 15 mM in trityl radical was prepared by dissolving 3.1 mg of the trityl radical tris-(8-carboxy-2,2,6,6-tetra-(hydroxyethoxy)-methylbenzo[1,2-d:4,5-d']-bis-(1,3-dithiol-4-yl)methyl sodium salt which was synthesized according to Example 29 in WO-A-97/09633 in 90 µl of $^{13}C_1$-pyruvic acid. Further, $GdCl_3$ (10 µl of a 10 mM aqueous solution) was added to the mixture to result in a composition being 1 mM in $Gd^{3+}$. The composition was mixed to homogeneity, placed in a probe cup and inserted in the DNP polariser. The composition was polarised under DNP conditions at 1.2 K in a 3.35 T magnetic field under irradiation with microwave (93.950 GHz). After 2 hours the polarisation was stopped.

The solid state polarisation was determined by solid state $^{13}C$-NMR as described in Example 1b to be 50%.

The addition of a paramagnetic metal ion to the composition to be polarised resulted in a solid state polarisation enhancement of about factor 2 in the sample.

Example 10

Comparison of the Solid State Polarisation of $^{13}C_1$-$D_2$-Fumarate with and without the Gd-Chelate of Example 4

Example 10a

Solid State Polarisation of $^{13}C_1$-$D_2$-Fumarate without Gd-Chelate of Example 4 (Comparison Example)

A composition being 10 mM in trityl radical was prepared by dissolving the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in a mixture of 0.21 mmol $^{13}C_1$-$D_2$-fumaric acid and 0.24 mmol TRIS dissolved in 17 µl water. The composition was mixed to homogeneity by a combination of vortex, light heating and ultrasound, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR carried out as described in Example 1b to be 220 (integral/mmol-13C).

Example 10b

Solid State Polarisation of $^{13}C_1$-$D_2$-Fumarate with Gd-Chelate of Example 4

In another experiment, a composition being 10 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.21 mmol $^{13}C_1$-$D_2$-fumaric acid and 0.24 mmol TRIS dissolved in 17 µl water. Further, the Gd-chelate of Example 4 was added to result in a composition being 0.7 mM in the Gd-chelate, i.e. 2.1 mM in $Gd^{3+}$. The composition was mixed to homogeneity, by a combination of vortex, light heating and ultrasound, and placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR as described in Example 1b to be 630 (integral/mmol-13C).

The addition of a paramagnetic metal ion resulted in a solid state polarisation enhancement of about a factor of 3.

Example 11

Production of a Solution of Hyperpolarised $^{13}C_1$-Fumarate with and without the Gd-Chelate of Example 4

Example 11a

Production of a Solution of Hyperpolarised $^{13}C_1$-Fumarate without the Gd-Chelate of Example 4 (Comparison Example)

The polarised solid composition of Example 10a was dissolved using a dissolution device according to WO-A-02/37132 in an aqueous solution of sodium hydroxide to provide a neutral solution of hyperpolarised TRIS-$^{13}C_1$-fumarate with a total fumarate concentration of about 40 mM in 40 mM TRIS buffer.

Liquid state polarisation was determined by liquid state $^{13}C$-NMR at 400 MHz to be 9%.

Example 11b

Production of a Solution of Hyperpolarised $^{13}C_1$-Fumarate with the Gd-Chelate of Example 4

The polarised solid composition of Example 10b was dissolved using a dissolution device according to WO-A-02/37132 in an aqueous solution of sodium hydroxide to provide a neutral solution of hyperpolarised TRIS-$^{13}C_1$-fumarate with a total fumarate concentration of about 40 mM in 40 mM TRIS buffer.

Liquid state polarisation was determined by liquid state $^{13}C$-NMR at 400 MHz to be 23%.

The addition of a paramagnetic metal ion resulted in a liquid state polarisation enhancement of a factor 2.5.

Example 12

Comparison of the Solid State Polarisation of $^{13}C_1$-Acetate with and without the Gd-Chelate of Example 4

Example 12a

Solid State Polarisation of $^{13}C_1$-Acetate without the Gd-Chelate of Example 4 (Comparison Example)

A composition being 10 mM in trityl radical was prepared by dissolving the trityl radical tris-(8-carboxy-2,2,6,6-tetra(hydroxyethoxy)methylbenzo[1,2-d:4,5-d']-bis-(1,3-dithiol-4-yl)methyl sodium salt which was synthesized according to Example 29 in WO-A-97/09633 in a mixture of 0.199 mmol TRIS-$^{13}C_1$-acetate and 13 µl water. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}C$-NMR carried out as described in Example 1b to be 195 (integral/mmol-13C).

Example 12b

Solid State Polarisation of $^{13}C_1$-Acetate with the Gd-Chelate of Example 4

A composition being 10 mM in trityl radical was prepared by dissolving the trityl radical tris-(8-carboxy-2,2,6,6-tetra(hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.199 mmol TRIS-$^{13}C_1$-acetate and 13 µl water. Further, the Gd-chelate of Example 4 was added to result in a composition being 0.2 mM in the Gd-chelate, i.e. 0.6 mM in $Gd^{3+}$. The composition was mixed to homogeneity, by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}$C-NMR as described in Example 1b to be 450 (integral/mmol-13C).

The addition of a paramagnetic metal ion resulted in a solid state polarisation enhancement of a factor 2.3.

Example 13

Comparison of the Solid State Polarisation of $^{13}$C$_1$-Bicarbonate with and without the Gd-Chelate of Example 4

Example 13a

Solid State Polarisation of $^{13}$C$_1$-Bicarbonate without the Gd-Chelate of Example 4 (Comparison Example)

A composition being 10 mM in trityl radical was prepared by dissolving the trityl radical tris(8-carboxy-2,2,6,6-tetra (hydroxyethoxy)methylbenzo[1,2-d:4,5-d']-bis-(1,3-dithiol-4-yl)methyl sodium salt which was synthesized according to Example 29 in WO-A-97/09633 in a mixture of 21 mg Cs-$^{13}$C$_1$-bicarbonate, 5 μl glycerol and 8 μl water. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}$C-NMR carried out as described in Example 1b to be 70 (integral/mmol-13C).

Example 13b

Solid State Polarisation of $^{13}$C$_1$-Bicarbonate with the Gd-Chelate of Example 4

A composition being 10 mM in trityl radical was prepared by dissolving the trityl radical tris-(8-carboxy-2,2,6,6-tetra (hydroxyethoxy)-methylbenzo[1,2-d:4,5-d']-bis-(1,3-dithiol-4-yl)methyl sodium salt which was synthesized according to Example 29 in WO-A-97/09633 in a mixture of 21 mg Cs-$^{13}$C$_1$-bicarbonate, 5 μl glycerol and 8 μl water. Further, the Gd-chelate of Example 4 was added to result in a composition being 0.7 mM in the Gd-chelate, i.e. 2.1 mM in Gd$^{3+}$. The composition was mixed to homogeneity, by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped.

The solid state polarisation was determined by solid state $^{13}$C-NMR as described in Example 1b to be 390 (integral/mmol-13C).

The addition of a paramagnetic metal ion resulted in a solid state polarisation enhancement of a factor 5.6.

Example 14

Comparison of the Solid State Polarisation of $^{13}$C$_1$-Lactate with and without the Gd-Chelate of Example 4

Example 14a

Solid State Polarisation of $^{13}$C$_1$-Lactate without the Gd-Chelate of Example 4 (Comparison Example)

A composition being 13 mM in trityl radical was prepared by dissolving the trityl radical tris-(8-carboxy-2,2,6,6-tetra (hydroxyethoxy)methylbenzo[1,2-d:4,5-d']-bis-(1,3-dithiol-4-yl)methyl sodium salt which was synthesized according to Example 29 in WO-A-97/09633 in 0.23 mmol $^{13}$C$_1$-lactate (57% water solution). The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 2 hours the polarisation was stopped.

The solid state polarisation was determined by solid state $^{13}$C-NMR carried out as described in Example 1b to be 28 (integral/mmol-13C).

Example 14b

Solid State Polarisation of $^{13}$C$_1$-Lactate with the Gd-Chelate of Example 4

A composition being 13 mM in trityl radical was prepared by dissolving the trityl radical tris-(8-carboxy-2,2,6,6-tetra (hydroxyethoxy)-methylbenzo[1,2-d:4,5-d']-bis-(1,3-dithiol-4-yl)methyl sodium salt which was synthesized according to Example 29 in WO-A-97/09633 in 0.23 mmol $^{13}$C$_1$-lactate (57% water solution). Further, the Gd-chelate of Example 4 was added to result in a composition being 0.4 mM in the Gd-chelate, i.e. 1.2 mM in Gd$^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHZ). After 2 hours the polarisation was stopped.

The solid state polarisation was determined by solid state $^{13}$C-NMR as described in Example 1b to be 178 (integral/mmol-13C).

The addition of a paramagnetic metal ion resulted in a solid state polarisation enhancement of a factor 6.4.

Example 15

Comparison of the Liquid State Polarisation of 3-Hydroxybutyrate with and without the Gd-Chelate of Example 4

Example 15a

Liquid State Polarisation of 3-Hydroxybutyrate without the Gd-Chelate of Example 4 (Comparison Example)

A composition being 13 mM in trityl radical was prepared by dissolving the trityl radical tris-(8-carboxy-2,2,6,6-tetra (hydroxyethoxy)methylbenzo[1,2-d:4,5-d']-bis-(1,3-dithiol-4-yl)methyl sodium salt which was synthesized according to Example 29 in WO-A-97/09633 in a mixture of 0.224 mmol 3-hydroxybutyrate (natural abundance $^{13}$C) and 15 µl water. The composition was mixed to homogeneity by a combination of vortex and light heating, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution of 20 mM phosphate buffer solution, pH 7.4, to provide a neutral solution of hyperpolarised 3-hydroxybutyrate with a total concentration of about 40 mM.

Liquid state polarisation was determined by liquid state $^{13}$C-NMR at 400 MHz to be 8%.

Example 15b

Liquid State Polarisation of 3-Hydroxybutyrate with the Gd-Chelate of Example 4

A composition being 13 mM in trityl radical was prepared by dissolving the trityl radical tris-(8-carboxy-2,2,6,6-tetra (hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.224 mmol 3-hydroxybutyrate (natural abundance $^{13}$C) and 15 µl water. Further, the Gd-chelate of Example 4 was added to result in a composition being 0.5 mM in the Gd-chelate, i.e. 1.5 mM in Gd$^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution of 20 mM phosphate buffer solution, pH 7.4, to provide a neutral solution of hyperpolarised 3-hydroxybutyrate with a total concentration of approximately 40 mM.

Liquid state polarisation was determined by liquid state $^{13}$C-NMR at 400 MHz to be 26%.

The addition of a paramagnetic metal ion resulted in a liquid state polarisation enhancement of more than a factor of 3.

Example 16

Liquid State Polarisation of TRIS-$^{13}$C$_1$-Glutamate with the Gd-Chelate of Example 4

A composition being 16 mM in trityl radical was prepared by dissolving the trityl radical tris-(8-carboxy-2,2,6,6-tetra (hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.06 mmol $^{13}$C$_1$-glutamic acid, 74 µmol TRIS and 7 µl water. Further, the Gd-chelate of Example 4 was added to result in a composition being 0.3 mM in the Gd-chelate, i.e. 0.9 mM in Gd$^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution to provide a neutral solution of hyperpolarised TRIS-$^{13}$C$_1$-glutamate with a total concentration of approximately 10 mM.

Liquid state polarisation was determined by liquid state $^{13}$C-NMR at 400 MHz to be 25%.

Example 17

Liquid State Polarisation of TRIS-$^{13}$C$_1$-Aspartate with the Gd-Chelate of Example 4

A composition being 16 mM in trityl radical was prepared by dissolving the trityl radical tris-(8-carboxy-2,2,6,6-tetra (hydroxyethoxy)-methylbenzo[1,2-d:4,5-d']-bis-(1,3-dithiol-4-yl)methyl sodium salt which was synthesized according to Example 29 in WO-A-97/09633 in a mixture of 0.058 mmol $^{13}$C$_1$-aspartic acid, 72 µmol TRIS and 7 µl water. Further, the Gd-chelate of Example 4 was added to result in a composition being 0.3 mM in the Gd-chelate, i.e. 0.9 mM in Gd$^{3+}$. The composition was mixed to homogeneity by a combination of vortex, light heating and sonication, placed in a probe cup and inserted in the DNP polariser. The composition was polarised under DNP conditions at 1.2 K in a 3.35 T magnetic field under irradiation with microwave (93.890 GHz). After 3 hours the polarisation was stopped and the composition was dissolved using a dissolution device according to WO-A-02/37132 in an aqueous solution to provide a neutral solution of hyperpolarised TRIS-$^{13}$C$_1$-aspartate with a total concentration of approximately 10 mM.

Liquid state polarisation was determined by liquid state $^{13}$C-NMR at 400 MHz to be 16%.

What is claimed is:

1. A hyperpolarised composition comprising a hyperpolarised endogenous $^{13}$C or $^{15}$N enriched compound, a carbon-based trityl radical and a gadolinium ion, wherein the composition is obtained by dynamic nuclear polarisation.

2. A polarising agent for use in dynamic nuclear polarisation of an endogenous $^{13}$C or $^{15}$N enriched compound, wherein the polarising agent comprises a carbon-based trityl radical and a gadolinium ion.

3. A method for producing a solid hyperpolarised endogenous $^{13}$C or $^{15}$N enriched compound, the method comprising the steps of preparing a composition comprising the endogenous $^{13}$C or $^{15}$N enriched compound, a carbon-based trityl radical and a gadolinium ion and carrying out dynamic nuclear polarisation on the composition.

4. A method for producing a liquid hyperpolarised endogenous $^{13}$C or $^{15}$N enriched compound, the method comprising the steps of preparing a composition comprising the endogenous $^{13}$C or $^{15}$N enriched compound or a precursor thereof, a carbon-based trityl radical and a gadolinium ion, carrying out dynamic nuclear polarisation on the composition, liquefying the composition by dissolution and optionally removing the trityl radical and/or the gadolinium ion from the liquefied composition.

* * * * *